US010919829B2

(12) United States Patent
Machida et al.

(10) Patent No.: US 10,919,829 B2
(45) Date of Patent: Feb. 16, 2021

(54) METHOD FOR PRODUCING ALCOHOL COMPOUND

(71) Applicant: KANEKA CORPORATION, Osaka (JP)

(72) Inventors: Koji Machida, Takasago (JP); Hiroaki Yasukouchi, Takasago (JP); Akira Nishiyama, Takasago (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 16/445,264

(22) Filed: Jun. 19, 2019

(65) Prior Publication Data
US 2019/0300465 A1 Oct. 3, 2019

Related U.S. Application Data

(63) Continuation of application No. PCT/JP2017/046877, filed on Dec. 27, 2017.

(30) Foreign Application Priority Data

Dec. 28, 2016 (JP) .............................. JP2016-254626

(51) Int. Cl.
C07C 37/74 (2006.01)
B01D 3/14 (2006.01)
B01D 15/36 (2006.01)
B01J 41/12 (2017.01)
C07C 37/56 (2006.01)
C07H 1/06 (2006.01)
C07D 249/08 (2006.01)
C07C 69/12 (2006.01)
C07C 33/22 (2006.01)
C07C 67/03 (2006.01)
C07B 61/00 (2006.01)

(52) U.S. Cl.
CPC ............. *C07C 37/74* (2013.01); *B01D 3/143* (2013.01); *B01D 15/363* (2013.01); *B01J 41/12* (2013.01); *C07C 33/22* (2013.01); *C07C 37/56* (2013.01); *C07C 67/03* (2013.01); *C07C 69/12* (2013.01); *C07D 249/08* (2013.01); *C07H 1/06* (2013.01); *C07B 61/00* (2013.01)

(58) Field of Classification Search
None
See application file for complete search history.

(56) References Cited

U.S. PATENT DOCUMENTS 4,948,915 A 8/1990 Keen
5,986,117 A * 11/1999 Cooper ................... C07C 67/03
554/149
2005/0085521 A1 4/2005 Suzuki et al.
2006/0014977 A1 * 1/2006 Miller ..................... C07C 67/03
560/179
2006/0217547 A1 * 9/2006 Maikap ................ C07H 13/08
536/28.3
2007/0208170 A1 9/2007 Maikap et al.

FOREIGN PATENT DOCUMENTS

| CN | 101045685 A | 10/2007 |
| CN | 102992956 A | 3/2013 |
| CN | 102993006 A * | 3/2013 |
| CN | 109384642 A * | 2/2019 |
| JP | 63-107949 | 5/1988 |
| JP | 2003-327578 | 11/2003 |
| JP | 2004-131462 | 4/2004 |
| JP | 2008-531680 | 8/2008 |

OTHER PUBLICATIONS

Written Opinion of the International Searching Authority (PCT/JP2017/046877) (2017) (Year: 2017).*
T. Ito et al., Continuous biodiesel production with anion-exchange resin, 11 Esteem Academic Journal, 26-34 (2015) (Year: 2015).*
M. Salunkhe et al., European Polymer Journal, 967-968 (1994) (Year: 1994).*
T. Tomasic et al., 5 Med. Chem. Commun. (2014) (Year: 2014).*
P. Wuts et al., Protection for the Hydroxyl Group, Including 1,2- and 1,3 Diols, in Greene's Protective Groups in Organic Synthesis, (4th ed., 2007) (Year: 2007).*
N. Shibasaki-Kitakawa et al., Bioresource Technology, 416-421 (2007) (Year: 2007).*
J. Otera, 93 Chemical Reviews, 1449-1470 (1993) (Year: 1993).*
X. Liu et al., 87 Fuel, 1076-1082 (2008) (Year: 2008).*
G. Zanoni et al., 12 Tetrahedron: Asymmetry, 1785-1792 (2001) (Year: 2001).*
M. Kajjout et al., 67 Tetrahedron, 4731-4741 (2011) (Year: 2011).*
H. Yasukouchi et al., 23 Organic Process Research & Development, 654-659 (2019) (Year: 2019).*
W. Pereira et al., The Journal of Organic Chemistry, 2032-2034 (1969) (Year: 1969).*
English-Language Machine Translation CN-102993006-A (2013) (Year: 2013).*
B. Xu et al., 41 International Journal of Chemical Kinetics, 101-106 (2009) (Year: 2009).*
J. Robertson et al., Selective Hydroxyl Protection and Deprotection, In Carbohydrates (Academic Press, 2003) (Year: 2003).*
English-Language Machine Translation CN-109384642-A (2019) (Year: 2019).*
R. Feuge et al., The Journal of the American Oil Chemists' Society, 97-102 (1949) (Year: 1949).*
Extended European Search Report dated Apr. 22, 2020, issued for the corresponding EP Application No. 17888899.6.
Junzo, Otera:"Transesterification", Chemical Reviews, vol. 93, No. 4, Jun. 1993(Jun. 1, 1993), pp. 1449-1470.

(Continued)

Primary Examiner — Alexander R Pagano
(74) Attorney, Agent, or Firm — Oblon, McClelland, Maier & Neustadt, L.L.P.

(57) ABSTRACT

A high-purity alcohol compound can be obtained by a method comprising passing a solution containing an ester compound and methanol and/or ethanol through a column packed with an anion exchange resin having methoxide and/or ethoxide as a counter anion to generate a methyl ester and/or ethyl ester, and distilling off the methyl ester and/or ethyl ester together with the methanol and/or ethanol.

16 Claims, No Drawings

(56) References Cited

OTHER PUBLICATIONS

International Search Report dated Feb. 6, 2018 in PCT/JP2017/046877, filed on Dec. 27, 2017.
Wuts, P, et al. Greene's Protective Groups in Organic Synthesis ($4^{th}$ edition), pp. 230-232.
Ito, T. et al. "Application of continuous process to production of biodiesels using methoxide type anion exchange resin", The Japanese Institute of Energy, 2011, pp. 72-73 ( with partial English translation).
Morimoto, Y. et al. "Study on the deactivation mechanism of the methoxide type anion exchange resin in the biodiesel production", Proceedings of College of Science and Technology Nihon University, 2012, pp. 1195-1196 (with Partial English Translation).
Morimoto, Y. et al. "Study on deactivation mechanism of methoxide type anion-exchange resin in consecutive biodiesel production using fixed-bed reactor", Proceedings of Japan Society of Material Cycles and waste Management, 2013, pp. 379-380 (with partial English Translation).

\* cited by examiner

METHOD FOR PRODUCING ALCOHOL COMPOUND

TECHNICAL FIELD

The present invention provides a method for obtaining an alcohol compound from an ester compound with high purity and by easy operation.

BACKGROUND ART

An alcohol compound is frequently used as a raw material, intermediate, and final product in the process of manufacturing pharmaceuticals, agricultural chemicals and the like. When an intended compound is synthesized through multiple stages, a hydroxyl group of an alcohol compound is protected using various protecting groups due to its high reactivity, and after that, the protecting group is removed at an appropriate stage. As a protecting group for the hydroxyl group, an acyl group is typically used since it is a protecting group resistant to acidic, weakly alkaline, oxidation, and reduction conditions. Therefore, it is an important subject to develop a simple method of protection by an acyl group and removal thereof for an alcohol compound. Thus, in addition to appropriate protection of the hydroxyl group, it is also important that deprotection can be performed easily.

As a method for producing an alcohol compound with high purity from an alcohol compound having a hydroxyl group protected with an acyl group, namely an ester compound, there are various known methods such as a method using potassium carbonate in a methanol-water mixed solvent, a method using sodium methoxide in methanol, a method using potassium cyanide in ethanol, a method using a phase-transfer catalyst and sodium hydroxide in water, a method using aqueous ammonia in methanol, a method using $BF_3 \cdot OEt_2$ in acetonitrile, a method using $Sc(OTf)_3$ in a methanol-water mixed solvent, a method using $Yb(OTf)_3$ in isopropanol, and a method using hydrazine in methanol (Non-Patent Document 1).

Hydrolysis is generally employed as a method for removing an acyl group from an alcohol compound protected by the acyl group, namely an ester compound.

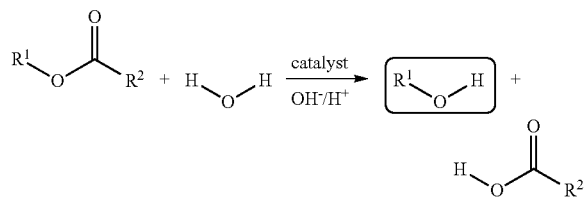

In addition, alcoholysis is also often employed as a method for removing an acyl group from an alcohol compound protected by the acyl group, namely an ester compound.

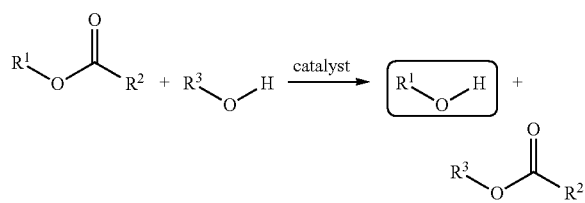

PRIOR ART DOCUMENT

Non-Patent Document

Non-Patent Document 1: Peter G. M. Wuts, & Thodora W. Greene. Greene's Protective Groups in Organic Synthesis (4th ed.), 230-232.

SUMMARY OF THE INVENTION

Problems to be Solved by the Invention

However, in the methods described in Non-Patent Document 1, when inorganic bases such as potassium carbonate, potassium cyanide, and sodium hydroxide are used, an extraction operation is required for separation from desired products. When ammonia or hydrazine is used, acyl groups that have been removed are converted to amides having a high boiling point, and hence column purification and crystallization are required for separation from desired products. Therefore, these methods cannot be regarded as easy considering a post-treatment.

Furthermore, in the method for removing an acyl group by hydrolysis, hydrolysis hardly proceeds without a catalyst, and hence a strong acid such as hydrochloric acid and sulfuric acid, or a strong alkali such as sodium hydroxide and potassium hydroxide is often used as a catalyst. In order to obtain an alcohol compound with high purity after the hydrolysis reaction, separation from the strong acid or strong alkaline catalyst used and a carboxylic acid as byproduct is required. Since a carboxylic acid generally has a high boiling point, it is not efficient to distill it off by concentration. For this reason, it is common to perform extraction of removing the carboxylic acid into an aqueous layer as a salt. However, in extraction, washing with water has to be repeated in many cases in order to remove the carboxylic acid and the used catalyst. In washing with water, there is no problem when the alcohol compound as a product is hydrophobic. However, when the alcohol compound as a product is hydrophilic, loss of the alcohol compound into the aqueous layer may occur, and it is thus necessary to repeat extraction more than once for the purpose of increasing a recovery ratio thereof. When the alcohol compound has a low boiling point, the alcohol compound is liable to volatilize to loss by vacuum distillation off of an extract. In addition, when a high water content has negative effect on the next reaction, it is necessary to perform concentration repeatedly for dehydration. Although hydrolysis reaction itself is very simple, a subsequent treatment is actually complicated, which has been a factor that significantly reduces productivity in an industrial-scale production.

Even in a method for removing an acyl group by alcoholysis, since a reaction does not proceed only by adding alcohol, Lewis acids such as aluminum chloride, boron trifluoride, and calcium chloride, or bases such as sodium alkoxide, potassium alkoxide, sodium carbonate, and potassium carbonate are often used as a catalyst. Moreover, it is necessary to add a large excess of alcohol to complete the reaction.

In order to obtain a desired alcohol compound with high purity after alcoholysis, the used catalyst must first be separated. Also in this case, a procedure in which water is added to a reaction solution to remove the catalyst into an aqueous layer and extract the alcohol compound is generally employed. Therefore, a complicated extraction operation has to be conducted as explained in the above hydrolysis. In addition, since the efficiency of extraction decreases due to the large excess of alcohol, the alcohol has to be distilled off under reduced pressure beforehand. Although removal of the catalyst by filtration can be considered, part of the catalyst is dissolved in the large excess of alcohol, and thus, it is practically difficult to remove the catalyst completely. In the method by alcoholysis, since an ester derived from an acyl protecting group is produced as a by-product, it is required to take separation from the alcohol compound into account. As described above, the method by alcoholysis cannot be also regarded as a good method from the viewpoint of productivity in industrial-scale production.

In view of the problems of the conventional techniques described above, an object to be achieved by the present invention is to establish a production process that is capable of obtaining an alcohol compound from an ester compound with high purity and by easy operation.

Solutions to the Problems

As a result of intensive studies for achieving the above object, the inventors have found that transesterification is conducted by passing a methanol and/or ethanol solution of an ester compound through a column packed with an anion exchange resin having methoxide and/or ethoxide as a counter anion, and then, a methyl ester and/or ethyl ester produced as a by-product and the methanol and/or ethanol used as a solvent are distilled off together, whereby an alcohol compound can be obtained as a concentrate with high purity.

That is, the present invention relates to a method for producing an alcohol compound having one or more features described below.

[1] A method for producing an alcohol compound, comprising:
passing a solution containing an ester compound and methanol and/or ethanol through a column packed with an anion exchange resin having methoxide and/or ethoxide as a counter anion to generate a methyl ester and/or ethyl ester; and
distilling off the methyl ester and/or ethyl ester together with the methanol and/or ethanol.

[2] A method for producing an alcohol compound from an ester compound formed by protecting an alcohol compound with an acyl group, comprising:
passing a solution containing the ester compound and methanol and/or ethanol through a column packed with an anion exchange resin having methoxide and/or ethoxide as a counter anion to decompose the ester compound into the alcohol compound and a methyl ester and/or ethyl ester containing the acyl group; and
distilling off the methyl ester and/or ethyl ester together with the methanol and/or ethanol.

[3] The method according to [1] or [2], wherein the alcohol compound has a boiling point of 170° C. or higher, and the methyl ester and/or ethyl ester has a boiling point of lower than 170° C.

[4] The method according to any of [1] to [3], wherein the alcohol compound is obtained with a purity of 80 wt % or more.

[5] The method according to any of [1] to [4],
wherein the ester compound is represented by the following formula (1):

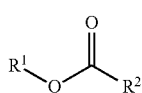

(1)

wherein $R^1$ is a substituted alkyl group having 1 or 2 carbon atoms, an optionally substituted alkyl group having 3 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms, and $R^2$ is a hydrogen atom, an optionally substituted alkyl group having 1 to 5 carbon atoms, an optionally substituted cycloalkyl group having 3 to 5 carbon atoms, or an optionally substituted alkenyl group having 2 to 5 carbon atoms, the methyl ester and/or ethyl ester is represented by the following formula (3):

wherein $R^2$ is the same as above, and $R^3$ is a methyl group or ethyl group, and the alcohol compound is represented by the following formula (2):

wherein $R^1$ is the same as above.

[6] The method according to [5], wherein $R^2$ is a hydrogen atom, methyl group, trifluoromethyl group, or tert-butyl group.

[7] The method according to any of [1] to [6], wherein the ester compound is (2R,3R)-2-difluorophenyl-3-pivaloyloxy-1-(1H-1,2,4-triazol-1-yl)-butan-2-ol, and the alcohol compound is (2R,3R)-2-difluorophenyl-1-(1H-1,2,4-triazol-1,3-butanediol.

[8] The method according to any of [1] to [7], wherein the ester compound is (2R,3R)-2-(2,4-difluorophenyl)-3-pivaloyloxy-1-(1H-1,2,4-triazol-1-yl)-butan-2-ol, and the alcohol compound is (2R,3R)-2-(2,4-difluorophenyl)-1-(1H-1,2,4-triazol-1-yl)-2,3-butanediol.

[9] The method according to any of [1] to [8], wherein an operational temperature during the passing of the solution containing the ester compound and methanol and/or ethanol is 0° C. or higher and 90° C. or lower.

[10] The method according to any of [1] to [9], wherein a space velocity (SV) of the solution containing the ester compound and methanol and/or ethanol is from 0.01 to 100 $hr^{-1}$.

[11] The method according to any of [1] to [10], wherein the total content of the ester compound, methanol, and ethanol is 80 mass % or more in the solution containing the ester compound and methanol and/or ethanol.

[12] The method according to any of [1] to [11], wherein the ester compound is contained in an amount of 5 mass % or less in 100 mass % of a solution obtained after passing through the column.

A method for producing an anion exchange resin having methoxide and/or ethoxide as a counter anion, comprising:
passing methanol and/or ethanol through a column packed with an anion exchange resin having a hydroxide ion as a counter anion.

[14] The method according to any of [1] to [12] using the anion exchange resin produced by the method according to [13].

EFFECT OF THE INVENTION

In the present invention, it is possible to efficiently produce a large amount of alcohol compound, which is useful as raw materials, intermediates, and final products of pharmaceuticals, agricultural chemicals and the like.

According to the production method of the present invention, a complicated extraction operation is unnecessary, and a high-purity alcohol compound can be obtained at a high yield by conducting a concentration operation only once. In addition, since a reaction is performed in a column, not only is a separation operation of an anion exchange resin after the reaction unnecessary but also the advantage of improvement of production efficiency afforded by continuous production can be enjoyed.

Mode for Carrying Out the Invention

The present invention will be described in detail below.

The ester compound used in the present invention is not particularly limited and may have one or more ester functional groups in the molecule thereof. The ester compound is preferably represented by the following formula (1):

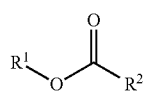

(1)

wherein $R^1$ is a substituted alkyl group having 1 or 2 carbon atoms, an optionally substituted alkyl group having 3 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms.

Examples of a substituent on $R^1$ include an optionally substituted aryl group having 6 to 10 carbon atoms such as phenyl or difluorophenyl; an optionally substituted heterocyclic group formed by removing one hydrogen atom from a heterocyclic ring (preferably a 3- to 10-membered ring, more preferably a 5- to 6-membered ring) composed of carbon and heteroelement (for example, nitrogen, oxygen, sulfur or the like), such as triazole or 3-acetamido-2,4,5-triacetoxytetrahydropyran; a halogen atom such as fluorine atom, chlorine atom, bromine atom, or iodine atom; a hydroxyl group; an alkoxy group (preferably having 1 to 10 carbon atoms) such as methoxy, ethoxy, phenoxy, or benzyloxy; an alkylthio group (preferably having 1 to 10 carbon atoms) such as methylthio; a halogenated alkyl group (preferably having 1 to 5 carbon atoms) such as trifluoromethyl; an acetyl group; a benzoyl group; a cyano group; a nitro group; a carboxy group; an amido group (preferably having 1 to 10 carbon atoms) such as acetylamino or benzoylamino; an acyl group (preferably having 1 to 10 carbon atoms) such as acetoxy or benzoyloxy; a monovalent group formed by removing a hydrogen atom from a compound having an ether bond (for example, a monovalent group formed from a cyclic ether such as 1,3-dioxane); an alkoxycarbonyl group (preferably having 1 to 10 carbon atoms) such as methoxycarbonyl or ethoxycarbonyl; a dialkylamino group (preferably having 1 to 10 carbon atoms) such as dimethylamino, diethylamino, or pyrrolidyl; and a protected amino group such as benzyloxycarbonylamino, tert-butylcarbonylamino, acetylamino, or benzoylamino. The optionally substituted heterocyclic group is preferable, and an optionally substituted nitrogen-containing or oxygen-containing heterocyclic group is more preferable. The number of substituents is not particularly limited.

The aryl group having 6 to 10 carbon atoms and the heterocyclic group exemplified as the substituent of $R^1$ each may have a halogen atom such as fluorine atom, chlorine atom, bromine atom, or iodine atom; a hydroxyl group; an alkoxy group (preferably having 1 to 10 carbon atoms) such as methoxy, ethoxy, phenoxy, or benzyloxy; an acetyl group; a benzoyl group; a cyano group; a nitro group; a carboxy group; an amido group (preferably having 1 to 10 carbon atoms) such as acetylamino or benzoylamino; an acyl group (preferably having 1 to 10 carbon atoms) such as acetoxy or benzoyloxy; an alkoxycarbonyl group (preferably having 1 to 10 carbon atoms) such as methoxycarbonyl or ethoxycarbonyl; a protected amino group such as benzyloxycarbonylamino, tert-butylcarbonylamino, acetylamino, or benzoylamino; or the like as a substituent. The number of substituents is not particularly limited.

As the alkyl group having 1 or 2 carbon atoms of $R^1$, methyl group or ethyl group can be given, and methyl group is preferable. As the substituent of the alkyl group having 1 or 2 carbon atoms, the optionally substituted heterocyclic group is more preferable.

As the alkyl group having 3 to 20 carbon atoms of $R^1$, an alkyl group having 3 to 10 carbon atoms is preferable, and an alkyl group having 3 to 6 carbon atoms is more preferable. As the substituent of the alkyl group having 3 to 20 carbon atoms, the optionally substituted aryl group having 6 to 10 carbon atoms and/or the optionally substituted heterocyclic group are more preferable.

As the cycloalkyl group having 3 to 20 carbon atoms of $R^1$, a cycloalkyl group having 3 to 10 carbon atoms is preferable, and a cycloalkyl group having 3 to 6 carbon atoms is more preferable.

As the alkenyl group having 2 to 20 carbon atoms of $R^1$, an alkenyl group having 2 to 10 carbon atoms is preferable, and an alkenyl group having 2 to 6 carbon atoms is more preferable.

As the aralkyl group having 7 to 20 carbon atoms of $R^1$, an aralkyl group having 7 to 10 carbon atoms is preferable, and a benzyl group is more preferable.

As the aryl group having 6 to 20 carbon atoms of $R^1$, an aryl group having 6 to 10 carbon atoms is preferable, and a phenyl group is more preferable.

As the heteroaryl group having 3 to 20 carbon atoms of $R^1$, a heteroaryl group having 3 to 10 carbon atoms is preferable.

$R^1$ is preferably the substituted alkyl group having 1 or 2 carbon atoms, the optionally substituted alkyl group having 3 to 20 carbon atoms, or the optionally substituted aralkyl group having 7 to 20 carbon atoms.

In the formula (1), $R^2$ is a hydrogen atom, an optionally substituted alkyl group having 1 to 5 carbon atoms, an optionally substituted cycloalkyl group having 3 to 5 carbon atoms, or an optionally substituted alkenyl group having 2 to 5 carbon atoms. Specific examples thereof include a hydrogen atom; a linear or branched alkyl group having 1 to 10 carbon atoms such as methyl, ethyl, n-propyl, isopropyl, tert-butyl, or n-pentyl; a halogenated alkyl group having 1 to 10 carbon atoms such as trifluoromethyl; an alkoxyalkyl group having 2 to 10 carbon atoms such as methoxymethyl or dimethoxymethyl; an alkyl cyanide group having 2 to 10 carbon atoms such as cyanomethyl; a cycloalkyl group having 3 to 10 carbon atoms such as cyclopropyl or cyclopentyl; and an alkenyl group having 2 to 10 carbon atoms such as vinyl or methallyl. $R^2$ is preferably hydrogen atom, methyl group, ethyl group, trifluoromethyl group, or tert-butyl group, and more preferably methyl group or tert-butyl group. When two or more different ester functional groups are included in the molecule, deprotection can be selectively conducted by appropriately adjusting a reaction temperature and/or residence time.

The ester compound (1) is preferably (2R,3R)-2-difluorophenyl-3-pivaloyloxy-1-(1H-1,2,4-triazol-1-yl)-butan-2-ol such as (2R,3R)-2-(2,4-difluorophenyl)-3-pivaloyloxy-1-(1H-1,2,4-triazol-1-yl)-butan-2-ol or (2R,3R)-2-(2,5-difluorophenyl)-3-pivaloyloxy-1-(1H-1,2,4-triazol-1-yl)-butan-2-ol, benzyl acetate, or pentaacetyl-β-D-glucosamine.

The alcohol compound obtained as a product of the present invention is not particularly limited and may have one or more hydroxyl groups in the molecule thereof. The alcohol compound preferably has a boiling point under atmospheric pressure of 170° C. or higher, more preferably 185° C. or higher, particularly preferably 200° C. or higher, and preferably 650° C. or lower. When the boiling point of the alcohol compound is high, it may be difficult to determine the boiling point by actual measurement. Thus, a calculated value may be used as appropriate in that case.

The alcohol compound is more preferably represented by the following formula (2):

(2)

wherein $R^1$ is the same as above. The alcohol compound (2) is preferably (2R,3R)-2-difluorophenyl-1-(1H-1,2,4-triazol-1-yl)-2,3-butanediol such as (2R,3R)-2-(2,4-difluorophenyl)-1-(1H-1,2,4-triazol-1-yl)-2,3-butanediol or (2R,3R)-2-(2,5-difluorophenyl)-1-(1H-1,2,4-triazol-1-yl)-2,3-butanediol, benzyl alcohol, or N-acetyl-β-D-glucosamine.

The methyl ester and/or ethyl ester produced as a by-product by transesterification in the present invention are not particularly limited since they depend on the structure of the ester compound used. The methyl ester and/or ethyl ester may have one or more methyl ester functional groups and/or ethyl ester functional groups in the molecule thereof. The methyl ester and/or ethyl ester preferably have a boiling point under atmospheric pressure of lower than 170° C., more preferably 150° C. or lower, particularly preferably 130° C. or lower, and preferably 30° C. or higher.

The methyl ester and/or ethyl ester is more preferably represented by the following formula (3):

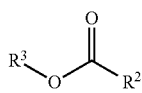

(3)

wherein $R^2$ is the same as above, and $R^3$ is methyl group or ethyl group. Specific examples of the methyl ester or ethyl ester (3) include methyl formate, ethyl formate, methyl acetate, ethyl acetate, methyl trifluoroacetate, ethyl trifluoroacetate, methyl methoxyacetate, ethyl methoxyacetate, methyl dimethoxyacetate, ethyl dimethoxyacetate, methyl cyanoacetate, ethyl cyanoacetate, methyl propionate, ethyl propionate, methyl butyrate, ethyl butyrate, methyl isobutyrate, ethyl isobutyrate, methyl pivalate, ethyl pivalate, methyl hexanoate, ethyl hexanoate, methyl cyclopropanecarboxylate, ethyl cyclopropanecarboxylate, methyl cyclopentanecarboxylate, ethyl cyclopentanecarboxylate, methyl acrylate, ethyl acrylate, methyl methacrylate, ethyl methacrylate, and the like. The methyl ester or ethyl ester (3) is preferably methyl formate, ethyl formate, methyl acetate, ethyl acetate, methyl trifluoroacetate, ethyl trifluoroacetate, methyl pivalate, or ethyl pivalate, and more preferably methyl acetate, ethyl acetate, methyl pivalate, or ethyl pivalate.

Next, the anion exchange resin used in the present invention will be described.

Examples of the anion exchange resin include strongly basic anion exchange resins and weakly basic anion exchange resins. From the viewpoint of improving a reaction rate, strongly basic anion exchange resins are preferable.

Strongly basic anionic resins are classified into type I and type II according to the structure of the ion exchange group. The type of a resin to be used in the present reaction is not particularly limited, and either the type I or the type II may be used.

Higher water retention capacity of the strongly basic anion exchange resin enables the improvement of a reaction rate of the present reaction. The water retention capacity is, for example, 40% or more, preferably 55% or more, more preferably 60% or more, particularly preferably 65% or more. Although the upper limit is not particularly limited, the water retention capacity is 90% or less.

As commercially-available products of the strongly basic anion exchange resin, for example, AMBERLITE (registered trademark) IRA900J (manufactured by Organo Corporation), IRA904 (same), IRA400J (same), IRA458RF (same), IRA410J (same), IRA910CT (same), IRA900(OH)-HG (same), ORLITE (registered trademark) DS-2 (same), DS-5 (same), DOWEX (registered trademark) 1×2 (manufactured by Dow Chemical Company), 1×8 (same), MONOSPHERE (registered trademark) 550A(OH) (same), DIAION (registered trademark) PA306S (manufactured by Mitsubishi Chemical Corporation), PA308 (same), HPA25L (same), PA312LOH (same), SA100H (same), and the like can be used. DOWEX (registered trademark) 1×2 or DIAION (registered trademark) PA306S is preferably used. These strongly basic anion exchange resins may be used singly or in combination of two or more. When these are used in combination of two or more, the mixing ratio thereof is not particularly limited. In the selection of the anion exchange resin, reactivity (which is generally affected by size of surface area, high water retention capacity, a low degree of crosslinking, and the like), particle size, price, and the like are preferably appropriately taken into consideration.

In the commercially-available products of the strongly basic anion exchange resin at the time of purchase, a counter anion is a chloride ion (Cl⁻ form), hydroxide ion (OH⁻ form), or the like. Therefore, in order to convert a counter anion to methoxide and/or ethoxide, a pretreatment for converting an anion exchange resin having a chloride ion (Cl⁻ form) or a hydroxide ion (OH⁻ form) as a counter anion into an anion exchange resin having methoxide and/or ethoxide as a counter anion has to be conducted.

When a counter anion is a chloride ion (Cl⁻ form), a replacement solution such as a methanol solution of lithium methoxide, sodium methoxide, potassium methoxide, calcium methoxide, magnesium methoxide or the like, or an ethanol solution of lithium ethoxide, sodium ethoxide, potassium ethoxide, calcium ethoxide, magnesium ethoxide or the like is preferably passed through an anion exchange resin having a chloride ion (Cl⁻ form) as a counter anion, thereby to produce an anion exchange resin having methoxide and/or ethoxide as a counter anion (pretreatment process 1). As the replacement solution, a methanol solution of sodium methoxide or an ethanol solution of sodium ethoxide is preferable, and a methanol solution of sodium methoxide is more preferable. These solutions may be used singly or in combination of two or more. When these solutions are used in combination of two or more, the mixing ratio thereof is not particularly limited.

The concentration of the replacement solution is not particularly limited as long as no solid precipitates. The lower limit of the concentration of the replacement solution is usually 0.01 mol/L, preferably 0.05 mol/L, more preferably 0.1 mol/L, and the upper limit thereof is 100 mol/L, preferably 50 mol/L, more preferably 20 mol/L.

As for the using amount of the replacement solution, a too large amount is not preferable in terms of cost, and a too small amount causes insufficient exchange of counter anions. Therefore, the lower limit of the using amount of the replacement solution is usually 0.1-fold volume, preferably 0.5-fold volume, more preferably 1.0-fold volume, and the upper limit thereof is 100-fold volume, preferably 50-fold volume, more preferably 30-fold volume, relative to the using amount of the anion exchange resin.

In the present method, before passing the replacement solution, it is also preferable to pass methanol and/or ethanol through the anion exchange resin having a chloride ion (Cl⁻ form) as a counter anion. By passing methanol and/or ethanol in advance, impurities derived from resin that dissolve in methanol and/or ethanol can be removed.

The using amount of the methanol and/or ethanol is preferably 0.1-fold volume or more, more preferably 1-fold volume or more, and preferably 100-fold volume or less, more preferably 30-fold volume or less, relative to the amount of the anion exchange resin having a chloride ion (Cl⁻ form) as a counter anion.

After the counter anion of the anion exchange resin is sufficiently exchanged to methoxide and/or ethoxide, methanol and/or ethanol are preferably further passed through the resin in order to remove excess solution. As for the using amount of the methanol and/or ethanol, a too large amount is not preferable in terms of cost, and a too small amount causes insufficient removal of inorganic salts. Therefore, the lower limit of the using amount of the methanol and/or ethanol is usually 0.1-fold volume, preferably 0.5-fold volume, more preferably 1.0-fold volume, and the upper limit thereof is 100-fold volume, preferably 50-fold volume, more preferably 30-fold volume, relative to the using amount of the anion exchange resin after the replacement solution has been passed through.

When a counter anion is a chloride ion (Cl⁻ form), first, an aqueous alkaline solution such as an aqueous lithium hydroxide solution, an aqueous sodium hydroxide solution, or an aqueous potassium hydroxide solution may be passed through an anion exchange resin having a chloride ion (Cl⁻ form) as a counter anion to convert the counter anion to a hydroxylate ion, thereby to produce an anion exchange resin having the hydroxide ion (OH⁻ form) as a counter anion. Subsequently, methanol and/or ethanol may be passed through the anion exchange resin having a hydroxide ion (OH⁻ form) as a counter anion through which the aqueous alkaline solution has been passed to convert the counter anion to methoxide and/or ethoxide, thereby to produce an anion exchange resin having methoxide and/or ethoxide as a counter anion (pretreatment process 2).

The concentration of the aqueous alkaline solution is not particularly limited as long as no solid precipitates. Usually, the lower limit of the concentration of the aqueous alkaline solution is 0.01 mol/L, preferably 0.05 mol/L, more preferably 0.1 mol/L, and the upper limit thereof is 100 mol/L, preferably 50 mol/L, more preferably 20 mol/L.

As for the using amount of the aqueous alkaline solution, a too large amount is not preferable in terms of cost, and a too small amount causes insufficient exchange of counter anions. Therefore, the lower limit of the using amount of the aqueous alkaline solution is usually 0.1-fold volume, preferably 0.5-fold volume, more preferably 1.0-fold volume, and the upper limit thereof is 100-fold volume, preferably 50-fold volume, more preferably 30-fold volume, relative to the using amount of the anion exchange resin.

As for the using amount of methanol and/or ethanol that is passed though the resin after passing the aqueous alkaline solution, a too large amount is not preferable in terms of cost, and a too small amount causes insufficient removal of inorganic salts. Therefore, the lower limit of the using amount of methanol and/or ethanol is usually 0.1-fold volume, preferably 0.5-fold volume, more preferably 1.0-fold volume, and the upper limit thereof is 100-fold volume, preferably 50-fold volume, more preferably 30-fold volume, relative to the using amount of the anion exchange resin through which the aqueous alkaline solution has been passed.

In the present method, before passing the aqueous alkaline solution, it is also preferable to pass water through the anion exchange resin having a chloride ion (Cl⁻ form) as a counter anion. By passing water in advance, impurities derived from resin dissolved in water can be removed.

The using amount of the water is preferably 0.1-fold volume or more, more preferably 1-fold volume or more, and preferably 100-fold volume or less, more preferably 30-fold volume or less, relative to the amount of the anion exchange resin having a chloride ion (Cl⁻ form) as a counter anion.

It is also desirable to pass water through the anion exchange resin after passing the aqueous alkaline solution through the anion exchange resin having a chloride ion (Cl⁻ form) and before passing methanol and/or ethanol through the anion exchange resin, thereby removing inorganic salts. A too small amount of the water used causes insufficient removal of inorganic salts. Therefore, the using amount of the water is preferably 0.1-fold volume or more, more preferably 1-fold volume or more, and preferably 100-fold volume or less, more preferably 30-fold volume or less, relative to the amount of the anion exchange resin through which the aqueous alkaline solution has been passed.

When a counter anion is a hydroxide ion (OH⁻ form), methanol and/or ethanol may be directly passed through an anion exchange resin having a hydroxide ion (OH⁻ form) as a counter anion to convert the counter anion to methoxide and/or ethoxide, thereby to produce an anion exchange resin having methoxide and/or ethoxide as a counter anion (pretreatment process 3). As for the using amount of the methanol and/or ethanol, a too large amount is not preferable in terms of cost, and a too small amount causes insufficient exchange of counter anions. Therefore, the lower limit of the using amount of the methanol and/or ethanol is usually 0.1-fold volume, preferably 0.5-fold volume, more preferably 1.0-fold volume, and the upper limit thereof is 100-fold volume, preferably 50-fold volume, more preferably 30-fold volume, relative to the using amount of the anion exchange resin.

In the present invention, from the viewpoint of operability, it is particularly desirable to use the anion exchange resin having methoxide and/or ethoxide as a counter anion that is produced by passing methanol and/or ethanol through a column packed with an anion exchange resin having a hydroxide ion as a counter anion.

It is preferable that a feeding rate of each liquid in a series of pretreatments be as high as possible from the viewpoint of improving productivity. However, if the feeding rate is too high, exchange of anions and washing of inorganic salts may become insufficient. Therefore, usually, the SV (space velocity) is preferably from 0.01 to 100 $hr^{-1}$, more preferably from 0.05 to 50 $hr^{-1}$, particularly preferably from 0.1 to 30 $hr^{-1}$. The operational temperature of the series of pretreatments is not particularly limited as long as the packed resin suffers no deterioration or the like. The operational temperature can be usually in a range up to about the boiling point of methanol and/or ethanol used and is preferably 90° C. or lower, more preferably 70° C. or lower, particularly preferably 60° C. or lower, and usually 0° C. or higher.

Next, a step of producing a desired alcohol compound by passing a solution containing the ester compound and methanol and/or ethanol through a column packed with the anion exchange resin having methoxide and/or ethoxide as a counter anion to generate a methyl ester and/or ethyl ester, and distilling off the methyl ester and/or ethyl ester together with the methanol and/or ethanol will be described. In other words, the present invention relates to a method for producing an alcohol compound from an ester compound formed by protecting an alcohol compound with an acyl group, and the method including: passing a solution containing the ester compound and methanol and/or ethanol through a column packed with the anion exchange resin having methoxide and/or ethoxide as a counter anion to decompose the ester compound into the alcohol compound and a methyl ester and/or ethyl ester containing the acyl group; and distilling off the methyl ester and/or ethyl ester together with the methanol and/or ethanol.

In the present invention, the "distilling off the methyl ester and/or ethyl ester together with the methanol and/or ethanol" means that the methyl ester and/or ethyl ester and the methanol and/or ethanol are distilled off together. More specifically, it means that the methyl ester and/or ethyl ester and the methanol and/or ethanol are distilled off together by a series of concentration operations.

The using amount of the methanol and/or ethanol is not particularly limited as long as the ester compound does not precipitate as a solid. The lower limit of the using amount of the methanol and/or ethanol is usually 0.1-fold weight, preferably 0.5-fold weight, more preferably 1-fold weight, and the upper limit thereof is 100-fold weight, preferably 50-fold weight, more preferably 20-fold weight, relative to the ester compound.

There is no need to use a reaction solvent because the methanol anchor ethanol also serves as a solvent. However, a reaction solvent may be mixed as appropriate for the purpose of adjusting the viscosity and liquid permeability of a solution. A solvent to be mixed is not particularly limited as long as it does not participate in the reaction, and specific examples thereof include an aliphatic hydrocarbon solvent such as n-hexane, cyclohexane or methylcyclohexane; an aromatic hydrocarbon solvent such as benzene, toluene, or xylene; an ether solvent such as diethyl ether, diisopropyl ether, tetrahydrofuran, methyltetrahydrofuran, methyl t-butyl ether, 1,4-dioxane, or cyclopentyl methyl ether; a halogenated solvent such as dichloromethane, 1,1,1-trichloroethane, or chlorobenzene; a ketone solvent such as acetone, methyl ethyl ketone, or methyl isobutyl ketone; a nitrile solvent such as acetonitrile, propionitrile, or butyronitrile; and an amide solvent such as N,N-dimethylformamide, N,N-dimethylacetamide, or N-methylpyrrolidone. These solvents may be used singly or in combination of two or more. When these solutions are used in combination of two or more, the mixing ratio thereof is not particularly limited. In the present invention, the content of the reaction solvent is preferably as small as possible from the viewpoint of purification. That is, in 100 mass % of the solution containing the ester compound and methanol and/or ethanol to be passed through the anion exchange resin having methoxide and/or ethoxide as a counter anion, the total content of the ester compound and the methanol and/or ethanol is preferably 80 mass % or more, more preferably 90 mass % or more, further preferably 95 mass % or more, particularly preferably 100 mass % (that is, the solution is composed of the ester compound and methanol and/or ethanol).

The using amount of the anion exchange resin is not particularly limited as long as the reaction proceeds, and is usually 0.001-fold weight or more, preferably 0.01-fold weight or more, more preferably 0.05-fold weight or more, and usually 200-fold weight or less, preferably 100-fold weight or less, more preferably 50-fold weight or less, relative to the ester compound.

The operational temperature during passing of the solution containing the ester compound and methanol and/or ethanol is not particularly limited as long as a packed resin suffers no deterioration or the like. The operational temperature can be usually in a range up to about the boiling point of methanol or ethanol used, and is preferably 90° C. or lower, more preferably 70° C. or lower, further preferably 60° C. or lower, particularly preferably 50° C. or lower, and usually 0° C. or higher, preferably 15° C. or higher, more preferably 30° C. or higher.

It is preferable that a feeding rate of the solution containing the ester compound and methanol and/or ethanol be as high as possible from the viewpoint of improving productivity. However, if the feeding rate is too high, transesterification may become insufficient. Therefore, usually, the SV (space velocity) is preferably from 0.01 to 100 $hr^{-1}$, more preferably from 0.05 to 50 $hr^{-1}$, particularly preferably from 0.1 to 30 $hr^{-1}$, even more preferably from 0.3 to 20 $hr^{-1}$, most preferably from 0.5 to 10 $hr^{-1}$.

The reaction is usually performed by standing a column packed with the anion exchange resin vertically and passing the methanol and/or ethanol solution of the ester compound through the column. The flowing direction of the solution is not particularly limited, and an upflow method or a downflow method can be used.

There are no specific restrictions on the above-mentioned column, and a material for the column may be appropriately selected depending on the demands for resistance to solvents and bases, pressure resistance, heat resistance, and the like. For example, metals such as iron, titanium, copper, nickel, chromium, and aluminum, alloys such as stainless steel, hastelloy, and Monel, glass, silicon, silicon carbide, various types of ceramics, peak resin, tetrafluoroethylene, and the like can be used.

A solution obtained after passing through the column by the above operations contains a desired alcohol compound, methanol and/or ethanol as a solvent, and a methyl ester and/or ethyl ester as a by-product. Since this solution does not contain a catalyst, a complicated extraction operation for removing a catalyst is unnecessary, and there is no worry of loss of the alcohol compound which is hydrophilic into an aqueous layer. Since the alcohol compound is a component with the highest boiling point among this mixture, concentration is performed by heating at atmospheric pressure, pressure reduction, heating at reduced pressure, or the like, so that the desired alcohol compound can be highly purified. The purity of the alcohol compound thus obtained is usually 80 wt % or more, preferably 90 wt % or more, more preferably 95 wt % or more. The larger the difference in boiling point between the desired alcohol compound and the methyl ester and/or ethyl ester produced as a by-product, the less the loss of the alcohol compound at the time of concentration, so that the yield is improved.

Furthermore, since the solution obtained after passing through the column contains almost no ester compound used as a raw material, it is easy to obtain the desired alcohol compound. In 100 mass % of the solution obtained after passing through the column, the content of the ester compound as a raw material is preferably 5 mass % or less, more preferably 3 mass % or less, further preferably 2 mass % or less, still more preferably 1 mass % or less, still further preferably 0.5 mass % or less, particularly preferably 0 mass %.

The desired product thus obtained has sufficient purity to be used in a subsequent step. In order to further increase the purity, a commonly used purification technique, such as crystallization, fractional distillation, column chromatography, or the like, may be used.

In addition, the anion exchange resin through which the solution containing the ester compound and methanol and/or ethanol has been passed has a reduced catalytic activity, so that it is difficult to use again as it is. In the present invention, the above-described pretreatment process 1 or 2 is conducted for the anion exchange resin through which the solution containing the ester compound and methanol and/or ethanol has been passed, whereby the anion exchange resin having methoxide and/or ethoxide as a counter anion can be regenerated to reuse. When regenerating the anion exchange resin, by replacing the "anion exchange resin having chloride ion (Cl$^-$ form) as a counter anion" in the pretreatment processes 1 and 2 with the "anion exchange resin through which the solution containing the ester compound and methanol and/or ethanol has been passed", the pretreatment process 1 or 2 can be appropriately applied.

This application claims benefit of priority based on Japanese Patent Application No. 2016-254626 filed on Dec. 28, 2016. The entire content of the specification of Japanese Patent Application No. 2016-254626 filed on Dec. 28, 2016 is incorporated herein by reference.

EXAMPLES

Hereinbelow, the present invention will be more specifically described in examples. These examples do not limit the present invention.

(1) Production of Benzyl Alcohol

Example 1

Into a column (Omnifit (registered trademark), inner diameter: 10 mm), 1.76 g (about 2.4 mL) of an anion exchange resin (DIAION (registered trademark) PA306S, Cl form) was packed, and the column was placed in a column oven whose temperature was adjusted to 25° C., stood vertically and fixed. Next, 25 mL of 1 mol/L sodium methoxide solution previously prepared was fed into the column at a rate of 0.16 mL/min (SV: 4 hr$^{-1}$) using a syringe pump (manufactured by YMC CO., LTD.). Next, 49 mL of methanol was fed into the column at a rate of 0.82 mL/min (SV: 20 hr$^{-1}$) using a syringe pump to wash the resin.

Subsequently, 17 g of methanol was added to 3 g of benzyl acetate to prepare a homogeneous solution, the prepared solution was passed through the column at a rate of 0.20 mL/min (SV: 5 hr$^{-1}$) using a syringe pump, and the reaction solution was collected from an outlet of the column. As a result, the reaction solution containing 2.12 g of desired benzyl alcohol (boiling point: 205° C.) was obtained (yield: 98%). In the obtained reaction solution, only methyl acetate (boiling point: 57° C.) was identified, and no acetic acid was identified. Although the reaction rate gradually decreased due to a long-time feeding, the resin was regenerated by feeding a sodium methoxide solution to the column after use, whereby the reaction rate was recovered to the initial reaction rate.

Example 2

Into a column (Omnifit (registered trademark), inner diameter: 10 mm), 1.61 g (about 2.4 mL) of an anion exchange resin (DIAION (registered trademark) PA308, Cl form) was packed, and the column was placed in a column oven whose temperature was adjusted to 25° C., stood vertically and fixed. Next, 25 mL of 1 mol/L sodium methoxide solution previously prepared was fed into the column at a rate of 0.16 mL/min (SV: 4 hr$^{-1}$) using a syringe pump (manufactured by YMC CO., LTD.). Next, 49 mL of methanol was fed into the column at a rate of 0.82 mL/min (SV: 20 hr$^{-1}$) using a syringe pump to wash the resin.

Subsequently, 17 g of methanol was added to 3 g of benzyl acetate to prepare a homogeneous solution, the prepared solution was passed through the column at a rate of 0.20 mL/min (SV: 5 hr$^{-1}$) using a syringe pump, and the reaction solution was collected from an outlet of the column. As a result, the reaction solution containing 1.94 g of desired benzyl alcohol was obtained (yield: 90%). It was possible to selectively remove methyl acetate produced as a by-product by concentration operation. In the obtained reaction solution, only methyl acetate was identified, and no acetic acid was identified. Although the reaction rate gradually decreased due to a long-time feeding, the resin was regenerated by feeding a sodium methoxide solution to the column after use, whereby the reaction rate was recovered to the initial reaction rate.

Example 3

Into a column (Omnifit (registered trademark), inner diameter: 10 mm), 1.60 g (about 2.4 mL) of an anion exchange resin (DIAION (registered trademark) HPA25L, Cl form) was packed, and the column was placed in a column oven whose temperature was adjusted to 25° C., stood vertically and fixed. Next, 25 mL of 1 mol/L sodium methoxide solution previously prepared was fed into the column at a rate of 0.16 mL/min (SV: 4 hr$^{-1}$) using a syringe pump (manufactured by YMC CO., LTD.). Next, 49 mL of methanol was fed into the column at a rate of 0.82 mL/min (SV: 20 hr$^{-1}$) using a syringe pump to wash the resin.

Subsequently, 17 g of methanol was added to 3 g of benzyl acetate to prepare a homogeneous solution, the prepared solution was passed through the column at a rate of 0.20 mL/min (SV: 5 hr$^{-1}$) using a syringe pump, and the reaction solution was collected from an outlet of the column. As a result, the reaction solution containing 1.84 g of desired benzyl alcohol was obtained (yield: 85%). It was possible to selectively remove methyl acetate produced as a by-product by concentration operation. In the obtained reaction solution, only methyl acetate was identified, and no acetic acid was identified. Although the reaction rate gradually decreased due to a long-time feeding, the resin was regenerated by feeding a sodium methoxide solution to the column after use, whereby the reaction rate was recovered to the initial reaction rate.

Example 4

Into a column (Omnifit (registered trademark), inner diameter: 10 mm), 1.56 g (about 2.4 mL) of an anion exchange resin (DOWEX (registered trademark) 1×2 100-200 Mesh, Cl form) was packed, and the column was placed in a column oven whose temperature was adjusted to 25° C., stood vertically and fixed. Next, 25 mL of 1 mol/L sodium methoxide solution previously prepared was fed into the column at a rate of 0.16 mL/min (SV: 4 hr$^{-1}$) using a syringe pump (manufactured by YMC CO., LTD.). Next, 49 mL of methanol was fed into the column at a rate of 0.82 mL/min (SV: 20 hr$^{-1}$) using a syringe pump to wash the resin.

Subsequently, 17 g of methanol was added to 3 g of benzyl acetate to prepare a homogeneous solution, the prepared solution was passed through the column at a rate of 0.20 mL/min (SV: 5 hr$^{-1}$) using a syringe pump, and the reaction solution was collected from an outlet of the column. As a result, the reaction solution containing 2.12 g of desired benzyl alcohol was obtained (yield: 98%). It was possible to selectively remove methyl acetate produced as a by-product by concentration operation. In the obtained reaction solution, only methyl acetate was identified, and no acetic acid was identified. Although the reaction rate gradually decreased due to a long-time feeding, the resin was regenerated by feeding a sodium methoxide solution to the column after use, whereby the reaction rate was recovered to the initial reaction rate.

Example 5

Into a column (Omnifit (registered trademark), inner diameter: 10 mm), 1.55 g (about 2.4 mL) of an anion exchange resin (DOWEX (registered trademark) 1×2 100-200 Mesh, Cl form) was packed, and the column was placed in a column oven whose temperature was adjusted to 60° C., stood vertically and fixed. Next, 60 mL of 1 mol/L sodium methoxide solution previously prepared was fed into the column at a rate of 1.0 mL/min (SV: 25 hr$^{-1}$) using a syringe pump (manufactured by YMC CO., LTD.). Next, 60 mL of methanol was fed into the column at a rate of 1.0 mL/min (SV: 25 hr$^{-1}$) using a syringe pump to wash the resin.

Subsequently, 34 g of methanol was added to 6 g of benzyl acetate to prepare a homogeneous solution, the prepared solution was passed through the column at a rate of 1.0 mL/min (SV: 25 hr$^{-1}$) using a syringe pump, and the reaction solution was collected from an outlet of the column. As a result, the reaction solution containing 4.28 g of desired benzyl alcohol was obtained (yield: 99%). It was possible to selectively remove methyl acetate produced as a by-product by concentration operation. In the obtained reaction solution, only methyl acetate was identified, and no acetic acid was identified. Although the reaction rate gradually decreased due to a long-time feeding, the resin was regenerated by feeding a sodium methoxide solution to the column after use, whereby the reaction rate was recovered to the initial reaction rate.

Example 6

Into a column (Omnifit (registered trademark), inner diameter: 10 mm), 1.84 g (about 2.9 mL) of an anion exchange resin (AMBERLITE (registered trademark) IRA900 (011)-HG, OH form) was packed, and the column was placed in a column oven whose temperature was adjusted to 25° C., stood vertically and fixed. Next, 10 mL of methanol was fed into the column at a rate of 0.19 mL/min (SV: 4 hr$^{-1}$) using a syringe pump (manufactured by YMC CO., LTD.) to wash the resin.

Subsequently, 17 g of methanol was added to 3 g of benzyl acetate to prepare a homogeneous solution, the prepared solution was passed through the column at a rate of 0.19 mL/min (SV: 4 hr$^{-1}$) using a syringe pump, and the reaction solution was collected from an outlet of the column. As a result, the reaction solution containing 1.86 g of desired benzyl alcohol was obtained (yield: 86%). It was possible to selectively remove methyl acetate produced as a by-product by concentration operation. In the obtained reaction solution, only methyl acetate was identified, and no acetic acid was identified. Although the reaction rate gradually decreased due to a long-time feeding, the resin was regenerated by feeding a sodium methoxide solution to the column after use, whereby the reaction rate was recovered to the initial reaction rate.

(2) Production of (2R,3R)-2-(2,4-difluorophenyl)-1-(1H-1,2,4-triazol-1-yl)-2,3-butanediol (5)

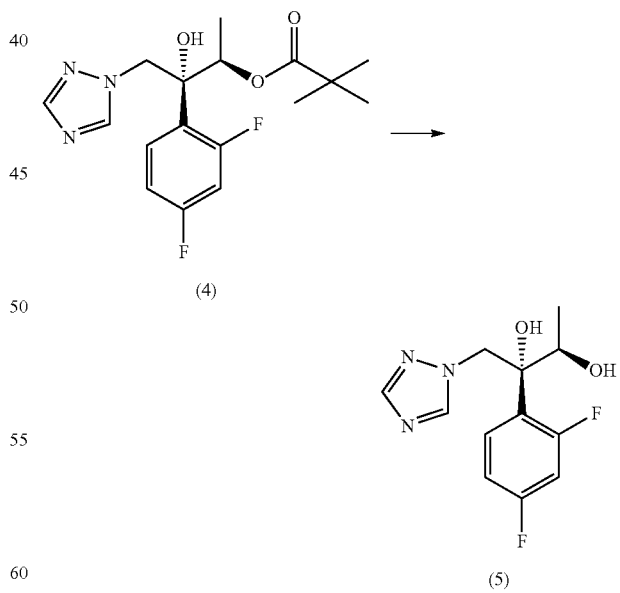

The alcohol compounds described in Examples 7 to 19 and the starting material products of Reference Examples 1 and 2 were analyzed by HPLC under the following conditions and quantified, and then the yields or the reaction conversion rates were calculated.

HPLC conditions
Column: SHISEIDO CAPCELLPAK C18 TYPE MG (250×4.6 mm)
  Mobile phase A: 0.1% phosphoric acid aqueous solution
  Mobile phase B: acetonitrile
  Flow rate: 1.0 mL/min
  Detection wavelength: UV 210 nm
  Column temperature: 30° C.
  Retention time: (2R,3R)-2-(2,4-difluorophenyl)-1-(1H-1,2,4-triazol-1-yl)-2,3-butanediol (5); 7.1 minutes, (2R,3R)-2-(2,4-difluorophenyl)-3-pivaloyloxy-1-(1H-1,2,4-triazol-1-yl)-butan-2-ol (4); 28.7 minutes, (2S,3R)-1-chloro-2-(2,4-difluorophenyl)-3-pivaloyloxybutan-2-ol (6); 38.0 minutes
  Gradient conditions

| Time (min) | Mobile phase A (%) | Mobile phase B (%) |
|---|---|---|
| 0 | 70 | 30 |
| 15 | 70 | 30 |
| 25 | 40 | 60 |
| 45 | 40 | 60 |
| 50 | 10 | 90 |
| 60 | 10 | 90 |
| 60.1 | 70 | 30 |

Example 7

Into a column (Omnifit (registered trademark), inner diameter: 10 mm), 2.50 g (about 3.9 mL) of an anion exchange resin (DOWEX (registered trademark) 1×2 100-200 Mesh, Cl form) was packed, and the column was placed in a column oven whose temperature was adjusted to 25° C., stood vertically and fixed. Next, 20 mL of 1 mol/L sodium methoxide solution previously prepared was fed into the column at a rate of 0.33 mL/min (SV: 5 hr$^{-1}$) using a syringe pump (manufactured by YMC CO., LTD.). Next, 20 mL of methanol was fed into the column at a rate of 0.33 mL/min (SV: 5 hr$^{-1}$) using a syringe pump to wash the resin.

Subsequently, 11.33 g of methanol was added to 2 g of the compound (4) to prepare a homogeneous solution, the temperature of the column oven was adjusted to 40° C., the prepared solution was passed through the column at a rate of 0.025 mL/min (SV: 0.4 hr$^{-1}$) using a syringe pump, and the reaction solution was collected from an outlet of the column. As a result, the reaction solution containing 1.40 g of desired compound (5) was obtained (yield: 92%). In the obtained reaction solution, only methyl pivalate (boiling point: 102° C.) was identified, and no pivalic acid was identified. It was possible to selectively remove the methyl pivalate produced as a by-product by concentration operation. Although the reaction rate gradually decreased due to a long-time feeding, the resin was regenerated by feeding a sodium methoxide solution to the column after use, whereby the reaction rate was recovered to the initial reaction rate.

Example 8

Into a column (Omnifit (registered trademark), inner diameter: 10 mm), 2.48 g (about 3.9 mL) of an anion exchange resin (DOWEX (registered trademark) 1×2 100-200 Mesh, Cl form) was packed, and the column was placed in a column oven whose temperature was adjusted to 40° C., stood vertically and fixed. Next, 20 mL of 1 mol/L sodium methoxide solution previously prepared was fed into the column at a rate of 0.33 mL/min (SV: 5 hr$^{-1}$) using a syringe pump (manufactured by YMC CO., LTD.). Next, 70 mL of methanol was fed into the column at a rate of 0.33 mL/min (SV: 5 hr$^{-1}$) using a syringe pump to wash the resin.

Subsequently, 36.83 g of methanol was added to 6.5 g of the compound (4) to prepare a homogeneous solution, the temperature of the column oven was adjusted to 40° C., the prepared solution was passed through the column at a rate of 0.025 mL/min (SV: 0.4 hr$^{-1}$) using a syringe pump, and the reaction solution was collected from an outlet of the column. As a result, the reaction solution containing 4.90 g of desired compound (5) was obtained (yield: 99%). In the obtained reaction solution, only methyl pivalate was identified, and no pivalic acid was identified. It was possible to selectively remove the methyl pivalate produced as a by-product by concentration operation. Although the reaction rate gradually decreased due to a long-time feeding, the resin was regenerated by feeding a sodium methoxide solution to the column after use, whereby the reaction rate was recovered to the initial reaction rate.

Example 9

Into a column (EYELA (registered trademark), inner diameter: 10 mm), 2.50 g (about 3.9 mL) of an anion exchange resin (DOWEX (registered trademark) 1×2 100-200 Mesh, Cl form) was packed, and the column was placed in a column oven whose temperature was adjusted to 25° C., stood vertically and fixed. Next, 8 mL of methanol was fed into the column at a rate of 0.26 mL/min (SV: 4 hr$^{-1}$) using a syringe pump (manufactured by YMC CO., LTD.). Next, 31 mL of 1 mol/L sodium methoxide solution previously prepared was fed into the column at a rate of 0.26 mL/min (SV: 4 hr$^{-1}$) using a syringe pump. Next, 79 mL of methanol was fed into the column at a rate of 0.66 mL/min (SV: 10 hr$^{-1}$) using a syringe pump to wash the resin.

Subsequently, 18.51 g of ethanol was added to 2.5 g of the compound (4) to prepare a homogeneous solution, the temperature of the column oven was adjusted to 75° C., the prepared solution was passed through the column at a rate of 0.33 mL/min (SV: 5 hr$^{-1}$) using a syringe pump, and the reaction solution was collected from an outlet of the column. As a result, the reaction solution containing 1.36 g of desired compound (5) was obtained (yield: 89%). In the obtained reaction solution, only methyl pivalate was identified, and no pivalic acid was identified. It was possible to selectively remove the methyl pivalate produced as a by-product by concentration operation. Although the reaction rate gradually decreased due to a long-time feeding, the resin was regenerated by feeding a sodium methoxide solution to the column after use, whereby the reaction rate was recovered to the initial reaction rate.

Example 10

Into a column (EYELA (registered trademark), inner diameter: 10 mm), 2.50 g (about 3.9 mL) of an anion exchange resin (DOWEX (registered trademark) 1×2 100-200 Mesh, Cl form) was packed, and the column was placed in a column oven whose temperature was adjusted to 25° C., stood vertically and fixed. Next, 8 mL of methanol was fed into the column at a rate of 0.26 mL/min (SV: 4 hr$^{-1}$) using a syringe pump (manufactured by YMC CO., LTD.). Next, 31 mL of 1 mol/L sodium methoxide solution previously prepared was fed into the column at a rate of 0.26 mL/min (SV: 4 hr$^{-1}$) using a syringe pump. Next, 79 mL of methanol was fed into the column at a rate of 0.66 mL/min (SV: 10 hr$^{-1}$) using a syringe pump to wash the resin.

Subsequently, 14.81 g of methanol was added to 2.0 g of the compound (4) to prepare a homogeneous solution, the temperature of the column oven was adjusted to 60° C., the prepared solution was passed through the column at a rate of 0.33 mL/min (SV: 5 hr$^{-1}$) using a syringe pump, and the reaction solution was collected from an outlet of the column. As a result, the reaction solution containing 1.48 g of desired compound (5) was obtained (yield: 97%). In the obtained reaction solution, only methyl pivalate was identified, and no pivalic acid was identified. It was possible to selectively remove the methyl pivalate produced as a by-product by concentration operation. Although the reaction rate gradually decreased due to a long-time feeding, the resin was regenerated by feeding a sodium methoxide solution to the column after use, whereby the reaction rate was recovered to the initial reaction rate.

Example 11

Into a column (EYELA (registered trademark), inner diameter: 10 mm), 2.50 g (about 3.9 mL) of an anion exchange resin (DOWEX (registered trademark) 1×2 100-200 Mesh, Cl form) was packed, and the column was placed in a column oven whose temperature was adjusted to 25° C., stood vertically and fixed. Next, 8 mL of methanol was fed into the column at a rate of 0.26 mL/min (SV: 4 hr$^{-1}$) using a syringe pump (manufactured by YMC CO., LTD.). Next, 31 mL of 1 mol/L sodium methoxide solution previously prepared was fed into the column at a rate of 0.26 mL/min (SV: 4 hr$^{-1}$) using a syringe pump. Next, 79 mL of methanol was fed into the column at a rate of 0.66 mL/min (SV: 10 hr$^{-1}$) using a syringe pump to wash the resin.

Subsequently, 14.81 g of methanol was added to 2.0 g of the compound (4) to prepare a homogeneous solution, the temperature of the column oven was adjusted to 50° C., the prepared solution was passed through the column at a rate of 0.33 mL/min (SV: 5 hr$^{-1}$) using a syringe pump, and the reaction solution was collected from an outlet of the column. As a result, the reaction solution containing 1.29 g of desired compound (5) was obtained (yield: 84%). In the obtained reaction solution, only methyl pivalate was identified, and no pivalic acid was identified. It was possible to selectively remove the methyl pivalate produced as a by-product by concentration operation. Although the reaction rate gradually decreased due to a long-time feeding, the resin was regenerated by feeding a sodium methoxide solution to the column after use, whereby the reaction rate was recovered to the initial reaction rate.

Example 12

Into a column (EYELA (registered trademark), inner diameter: 10 mm), 2.50 g (about 3.9 mL) of an anion exchange resin (DOWEX (registered trademark) 1×2 100-200 Mesh, Cl form) was packed, and the column was placed in a column oven whose temperature was adjusted to 25° C., stood vertically and fixed. Next, 8 mL of methanol was fed into the column at a rate of 0.26 mL/min (SV: 4 hr$^{-1}$) using a syringe pump (manufactured by YMC CO., LTD.). Next, 31 mL of 1 mol/L sodium methoxide solution previously prepared was fed into the column at a rate of 0.26 mL/min (SV: 4 hr$^{-1}$) using a syringe pump. Next, 79 mL of methanol was fed into the column at a rate of 0.66 mL/min (SV: 10 hr$^{-1}$) using a syringe pump to wash the resin.

Subsequently, 14.81 g of methanol was added to 2.0 g of the compound (4) to prepare a homogeneous solution, the temperature of the column oven was adjusted to 50° C., the prepared solution was passed through the column at a rate of 0.065 mL/min (SV: 1 hr$^{-1}$) using a syringe pump, and the reaction solution was collected from an outlet of the column. As a result, the reaction solution containing 1.52 g of desired compound (5) was obtained (yield: 100%). In the obtained reaction solution, only methyl pivalate was identified, and no pivalic acid was identified. It was possible to selectively remove the methyl pivalate produced as a by-product by concentration operation. Although the reaction rate gradually decreased due to a long-time feeding, the resin was regenerated by feeding a sodium methoxide solution to the column after use, whereby the reaction rate was recovered to the initial reaction rate.

Example 13

Into a column (EYELA (registered trademark), inner diameter: 10 mm), 2.50 g (about 3.9 mL) of an anion exchange resin (DOWEX (registered trademark) 1×2 100-200 Mesh, Cl form) was packed, and the column was placed in a column oven whose temperature was adjusted to 25° C., stood vertically and fixed. Next, 8 mL of methanol was fed into the column at a rate of 0.26 mL/min (SV: 4 hr$^{-1}$) using a syringe pump (manufactured by YMC CO., LTD.). Next, 31 mL of 1 mol/L sodium methoxide solution previously prepared was fed into the column at a rate of 0.26 mL/min (SV: 4 hr$^{-1}$) using a syringe pump. Next, 79 mL of methanol was fed into the column at a rate of 0.66 mL/min (SV: 10 hr$^{-1}$) using a syringe pump to wash the resin.

Subsequently, 14.81 g of methanol was added to 2.0 g of the compound (4) to prepare a homogeneous solution, the temperature of the column oven was adjusted to 50° C., the prepared solution was passed through the column at a rate of 0.131 mL/min (SV: 2 hr$^{-1}$) using a syringe pump, and the reaction solution was collected from an outlet of the column. As a result, the reaction solution containing 1.51 g of desired compound (5) was obtained (yield: 99%). In the obtained reaction solution, only methyl pivalate was identified, and no pivalic acid was identified. It was possible to selectively remove the methyl pivalate produced as a by-product by concentration operation. Although the reaction rate gradually decreased due to a long-time feeding, the resin was regenerated by feeding a sodium methoxide solution to the column after use, whereby the reaction rate was recovered to the initial reaction rate.

Example 14

Into a column (EYELA (registered trademark), inner diameter: 10 mm), 2.96 g (about 3.9 mL) of an anion exchange resin (DIAION (registered trademark) PA306S, Cl form) was packed, and the column was placed in a column oven whose temperature was adjusted to 25° C., stood vertically and fixed. Next, 8 mL of methanol was fed into the column at a rate of 0.26 mL/min (SV: 4 hr$^{-1}$) using a syringe pump (manufactured by YMC CO., LTD.). Next, 31 mL of 1 mol/L sodium methoxide solution previously prepared was fed into the column at a rate of 0.26 mL/min (SV: 4 hr$^{-1}$) using a syringe pump. Next, 79 mL of methanol was fed into the column at a rate of 0.66 mL/min (SV: 10 hr$^{-1}$) using a syringe pump to wash the resin.

Subsequently, 14.81 g of methanol was added to 2.0 g of the compound (4) to prepare a homogeneous solution, the temperature of the column oven was adjusted to 50° C., the prepared solution was passed through the column at a rate of 0.065 mL/min (SV: 1 hr$^{-1}$) using a syringe pump, and the reaction solution was collected from an outlet of the column.

As a result, the reaction solution containing 1.50 g of desired compound (5) was obtained (yield: 98%). In the obtained reaction solution, only methyl pivalate was identified, and no pivalic acid was identified. It was possible to selectively remove the methyl pivalate produced as a by-product by concentration operation. Although the reaction rate gradually decreased due to a long-time feeding, the resin was regenerated by feeding a sodium methoxide solution to the column after use, whereby the reaction rate was recovered to the initial reaction rate.

Example 15

Into a column (Omnifit (registered trademark), inner diameter: 10 mm), 2.50 g (about 3.9 mL) of an anion exchange resin (DOWEX (registered trademark) 1×2 100-200 Mesh, Cl form) was packed, and the column was placed in a column oven whose temperature was adjusted to 25° C., stood vertically and fixed. Next, 8 mL of methanol was fed into the column at a rate of 0.26 mL/min (SV: 4 hr$^{-1}$) using a syringe pump (manufactured by YMC CO., LTD.). Next, 31 mL of 1 mol/L sodium methoxide solution previously prepared was fed into the column at a rate of 0.26 mL/min (SV: 4 hr$^{-1}$) using a syringe pump. Next, 79 mL of methanol was fed into the column at a rate of 0.66 mL/min (SV 10 hr$^{-1}$) using a syringe pump to wash the resin.

Subsequently, 14.81 g of methanol was added to 2.0 g of the compound (4) to prepare a homogeneous solution, the temperature of the column oven was adjusted to 40° C., the prepared solution was passed through the column at a rate of 0.065 mL/min (SV: 1 hr$^{-1}$) using a syringe pump, and the reaction solution was collected from an outlet of the column. As a result, the reaction solution containing 1.42 g of desired compound (5) was obtained (yield: 94%). In the obtained reaction solution, only methyl pivalate was identified, and no pivalic acid was identified. It was possible to selectively remove the methyl pivalate produced as a by-product by concentration operation. Although the reaction rate gradually decreased due to a long-time feeding, the resin was regenerated by feeding a sodium methoxide solution to the column after use, whereby the reaction rate was recovered to the initial reaction rate.

Example 16

Into a column (Omnifit (registered trademark), inner diameter: 10 mm), 2.96 g (about 3.9 mL) of an anion exchange resin (DIAION (registered trademark) PA306S, Cl form) was packed, and the column was placed in a column oven whose temperature was adjusted to 25° C., stood vertically and fixed. Next, 8 mL of methanol was fed into the column at a rate of 0.26 mL/min (SV: 4 hr$^{-1}$) using a syringe pump (manufactured by YMC CO., LTD.). Next, 31 mL of 1 mol/L sodium methoxide solution previously prepared was fed into the column at a rate of 0.26 mL/min (SV: 4 hr$^{-1}$) using a syringe pump. Next, 79 mL of methanol was fed into the column at a rate of 0.66 mL/min (SV: 10 hr$^{-1}$) using a syringe pump to wash the resin.

Subsequently, 14.81 g of methanol was added to 2.0 g of the compound (4) to prepare a homogeneous solution, the temperature of the column oven was adjusted to 40° C., the prepared solution was passed through the column at a rate of 0.065 mL/min (SV: 1 hr$^{-1}$) using a syringe pump, and the reaction solution was collected from an outlet of the column. As a result, the reaction solution containing 1.36 g of desired compound (5) was obtained (yield: 89%). In the obtained reaction solution, only methyl pivalate was identified, and no pivalic acid was identified. It was possible to selectively remove the methyl pivalate produced as a by-product by concentration operation. Although the reaction rate gradually decreased due to a long-time feeding, the resin was regenerated by feeding a sodium methoxide solution to the column after use, whereby the reaction rate was recovered to the initial reaction rate.

Example 17

Into a jacketed column (KIRIYAMA, inner diameter: 22 mm), 150.46 g (about 197.67 mL) of an anion exchange resin (DIAION (registered trademark) PA306S, Cl form) was packed, the temperature of the jacket was adjusted to 25° C., the column was stood vertically and fixed. Next, 198 mL of water was fed into the column at a rate of 3.29 mL/min (SV: 1 hr$^{-1}$) using a diaphragm pump (manufactured by KNF Co.). Next, 494 mL of 1 mol/L aqueous sodium hydroxide solution previously prepared was fed into the column at a rate of 3.29 mL/min (SV: 1 hr$^{-1}$) using a diaphragm pump. Next, 890 mL of water was fed into the column at a rate of 3.29 mL/min (SV: 1 hr$^{-1}$) using a diaphragm pump. Next, 890 mL of methanol was fed into the column at a rate of 3.29 mL/min (SV: 1 hr$^{-1}$) using a diaphragm pump to wash the resin.

Subsequently, 235.8 g of methanol was added to 42.4 g of the compound (4) to prepare a homogeneous solution, the temperature of the jacket was adjusted to 50° C., the prepared solution was passed through the column at a rate of 3.29 mL/min (SV: 1 hr$^{-1}$) using a diaphragm pump, and the reaction solution was collected from an outlet of the column. As a result, the reaction solution containing 31.96 g of desired compound (5) was obtained (yield: 99%). In the obtained reaction solution, only methyl pivalate was identified, and no pivalic acid was identified. It was possible to selectively remove the methyl pivalate produced as a by-product by concentration operation. Although the reaction rate gradually decreased due to a long-time feeding, the resin was regenerated by feeding an aqueous sodium hydroxide solution to the column after use, whereby the reaction rate was recovered to the initial reaction rate.

Example 18

Into a jacketed column (KIRIYAMA, inner diameter: 11 mm), 23.7 g (about 31.2 mL) of an anion exchange resin (DIAION (registered trademark) PA306S, Cl form) was packed, the temperature of the jacket was adjusted to 25° C., the column was stood vertically and fixed. Next, 31 mL of water was fed into the column at a rate of 0.52 mL/min (SV: 1 hr$^{-1}$) using a diaphragm pump (manufactured by KNF Co.). Next, 78.3 mL of 1 mol/L aqueous sodium hydroxide solution previously prepared was fed into the column at a rate of 0.52 mL/min (SV: 1 hr$^{-1}$) using a diaphragm pump. Next, 140.9 mL of water was fed into the column at a rate of 0.52 mL/min (SV: 1 hr$^{-1}$) using a diaphragm pump. Next, 281.7 mL of methanol was fed into the column at a rate of 1.04 mL/min (SV: 2 hr$^{-1}$) using a diaphragm pump to wash the resin.

Subsequently, 651.3 g of methanol was added to 120.3 g of the compound (4) to prepare a homogeneous solution, the temperature of the jacket was adjusted to 50° C., the prepared solution was passed through the column at a rate of 1.04 mL/min (SV: 2 hr$^{-1}$) using a diaphragm pump, and the reaction solution was collected from an outlet of the column. As a result, the reaction solution containing 88.02 g of desired compound (5) was obtained (yield: 96%). In the obtained reaction solution, only methyl pivalate was identified, and no pivalic acid was identified. It was possible to selectively remove the methyl pivalate produced as a by-product by concentration operation. Although the reaction rate gradually decreased due to a long-time feeding, the resin was regenerated by feeding an aqueous sodium hydroxide solution to the column after use, whereby the reaction rate was recovered to the initial reaction rate.

Example 19

Durability Evaluation of an Anion Exchange Resin

Into a column (EYELA (registered trademark), inner diameter: 10 mm), 2.96 g (about 3.9 mL) of an anion exchange resin (DIAION (registered trademark) PA306S, Cl form) was packed, and the column was placed in a column oven whose temperature was adjusted to 25° C., stood vertically and fixed. Next, 9.8 mL of 1 mol/L aqueous sodium hydroxide solution previously prepared was fed into the column at a rate of 0.26 mL/min (SV: 4 hr$^{-1}$) using a syringe pump (manufactured by YMC CO., LTD.). Next, 11.8 mL of water was fed into the column at a rate of 0.66 mL/min (SV: 10 hr$^{-1}$) using a syringe pump. Next, 17.7 mL of methanol was fed into the column at a rate of 0.66 mL/min (SV: 10 hr$^{-1}$) using a syringe pump to wash the resin.

Subsequently, 841.43 g of methanol was added to 145 g of the compound (4) to prepare a homogeneous solution, the temperature of the column oven was adjusted to 50° C., the prepared solution was passed through the column at a rate of 0.065 mL/min (SV: 1 hr$^{-1}$) using a syringe pump (feeding time: 163 hours). During the feeding, the reaction solution was appropriately sampled from an outlet of the column, and the reaction conversion rates were measured, whereby the following results were obtained. The reaction conversion rates were calculated based on the following formula from the HPLC analysis results of the sampled reaction solutions.

Reaction conversion rate=area value of compound (5)/(area value of compound (4)+area value of compound (5))×100[%]

TABLE 1

| Reaction time (hr) | 18 | 47 | 66 | 94 | 158 | 163 |
|---|---|---|---|---|---|---|
| Reaction conversion rate (%) | 99.9 | 99.7 | 99.4 | 98.2 | 66.7 | 55.9 |

Next, into the column containing the resin through which the reaction solution had been passed for 163 hours, 9.8 mL of 1 mol/L aqueous sodium hydroxide solution previously prepared was fed at a rate of 0.26 mL/min (SV: 4 hr$^{-1}$) using a syringe pump. Next, 11.8 mL of water was fed into the column at a rate of 0.66 mL/min (SV: 10 hr$^{-1}$) using a syringe pump. Next, 17.7 mL of methanol was fed into the column at a rate of 0.66 mL/min (SV: 10 hr$^{-1}$) using a syringe pump to wash the resin.

Subsequently, a methanol solution (14.7 wt %) of the compound (4) was passed through the column (50° C.) at a rate of 0.065 mL/min (SV: 1 hr$^{-1}$) using a syringe pump. As a result of analyzing the reaction solution sampled from an outlet of the column, the reaction conversion rate was found to be improved to 99.9%.

(3) Production of N-acetyl-β-D-glucosamine (8)

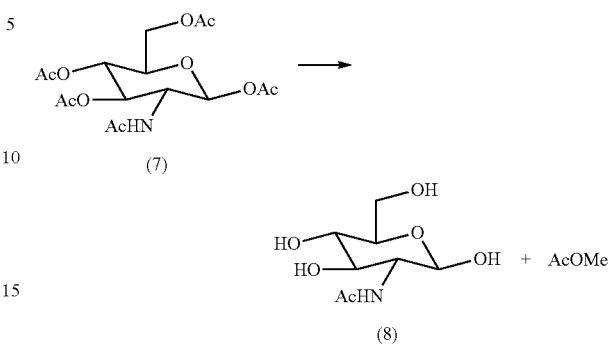

Example 20

Into a column (EYELA (registered trademark), inner diameter: 10 mm), 3.0 g (about 3.9 mL) of an anion exchange resin (DIAION (registered trademark) PA306S, Cl form) was packed, and the column was placed in a column oven whose temperature was adjusted to 25° C., stood vertically and fixed. Next, 12 mL of 1N aqueous NaOH solution was fed into the column at a rate of 0.065 mL/min (SV: 1 hr$^{-1}$) using a syringe pump (manufactured by YMC CO., LTD.). Next, 22 mL of water was fed into the column at a rate of 0.13 mL/min (SV: 2 hr$^{-1}$) using a syringe pump to wash the resin. Next, 19 mL of methanol was fed into the column at a rate of 0.13 mL/min (SV: 2 hr$^{-1}$) using a syringe pump to obtain a methoxide-form resin.

Subsequently, 50.0 g of methanol was added to 0.73 g of pentaacetyl-β-D-glucosamine (7) to prepare a homogeneous solution, the temperature of the column oven was adjusted to 50° C., the prepared solution was passed through the column at a rate of 0.13 mL/min (SV: 2 hr$^{-1}$) using a syringe pump, and the reaction solution was collected from an outlet of the column. As a result, the reaction solution containing 0.27 g of desired compound (8) (boiling point: 595° C., calculated using Advanced Chemistry Development (ACD/Labs) Software V11.02) was obtained (yield: 65%). In the obtained reaction solution, only methyl acetate was identified, and no acetic acid was identified. It was possible to selectively remove the methyl acetate produced as a by-product by concentration operation. Although the reaction rate gradually decreased due to a long-time feeding, the resin was regenerated by feeding an aqueous NaOH solution, water, and then methanol to the column after use, whereby the reaction rate was recovered to the initial reaction rate.

Reference Example 1

Production of (2R,3R)-2-(2,4-difluorophenyl)-3-pivaloyloxy-1-(1H-1,2,4-triazol-1-yl)-butan-2-ol (4)

Into a flask, 30 g of (2S,3R)-1-chloro-2-(2,4-difluorophenyl)-3-pivaloyloxybutan-2-ol (6), 9.04 g of triazole, and 90 g of DMA were added and completely dissolved, and the temperature of this solution was adjusted to 55° C. Then, 34.17 g of DBU was added dropwise to the flask slowly, and the mixture was stirred at the same temperature for 12 hours. Thereafter, the reaction solution was cooled to 25° C., 150 g of toluene and 60 g of water were added thereto for extraction, and the obtained organic layer was washed twice with further 60 g of water. The organic layer was concentrated under reduced pressure, and 42.45 g of a concentrate containing 24.79 g of the compound (4) was obtained (yield: 75%).

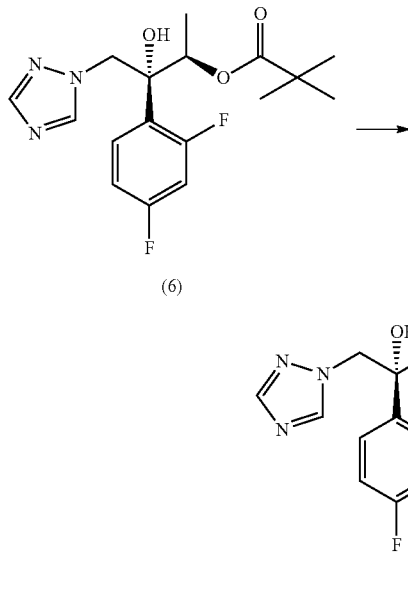

(6)

→

(4)

Reference Example 2

Production of (2R,3R)-2-(2,4-difluorophenyl)-1-(1H-1,2,4-triazol-1-yl)-2,3-butanediol (5)

The concentrate (pure content: 19.76 g) obtained in the above Reference Example 1, 13.83 g of toluene, and 25.69 g of THF were added into a flask, and the temperature of this solution was adjusted to 40° C. To the flask, 28% sodium methoxide/methanol solution was added dropwise slowly, and the mixture was stirred at the same temperature for 2 hours. Next, the reaction solution was separated by adding 29.64 g of water to thereby obtain 80.9 g of organic layer containing 14.0 g of the compound (5) (yield: 93%). The loss of the compound (5) into an aqueous layer was 1.2 g (8%).

The invention claimed is:

1. A method for producing an alcohol compound, the method comprising:
passing a solution comprising an ester compound and methanol and/or ethanol through a column packed with an anion exchange resin having methoxide and/or ethoxide as a counter anion such that a methyl ester and/or ethyl ester is generated; and
distilling off the methyl ester and/or ethyl ester together with the methanol and/or ethanol.

2. A method for producing an alcohol compound from an ester compound formed by protecting the alcohol compound with an acyl group, the method comprising:
passing a solution comprising the ester compound and methanol and/or ethanol through a column packed with an anion exchange resin having methoxide and/or ethoxide as a counter anion such that the ester compound is decomposed into the alcohol compound and a methyl ester and/or ethyl ester comprising the acyl group; and distilling off the methyl ester and/or ethyl ester together with the methanol and/or ethanol.

3. The method according to claim 1, wherein the alcohol compound has a boiling point of 170° C. or higher, and the methyl ester and/or ethyl ester has a boiling point of lower than 170° C.

4. The method according to claim 1, wherein the alcohol compound is obtained with a purity of 80 wt % or more.

5. The method according to claim 1, wherein the ester compound is represented by the following formula (1):

(1)

wherein $R^1$ is a substituted alkyl group having 1 or 2 carbon atoms, an optionally substituted alkyl group having 3 to 20 carbon atoms, an optionally substituted cycloalkyl group having 3 to 20 carbon atoms, an optionally substituted alkenyl group having 2 to 20 carbon atoms, an optionally substituted aralkyl group having 7 to 20 carbon atoms, an optionally substituted aryl group having 6 to 20 carbon atoms, or an optionally substituted heteroaryl group having 3 to 20 carbon atoms, and $R^2$ is a hydrogen atom, an optionally substituted alkyl group having 1 to 5 carbon atoms, an optionally substituted cycloalkyl group having 3 to 5 carbon atoms, or an optionally substituted alkenyl group having 2 to 5 carbon atoms, the methyl ester and/or ethyl ester is represented by the following formula (3):

(3)

wherein $R^2$ is the same as in the formula (1), and $R^3$ is a methyl group or ethyl group, and
the alcohol compound is represented by the following formula (2):

(2)

wherein $R^1$ is the same as in the formula (1).

6. The method according to claim 5, wherein $R^2$ is a hydrogen atom, methyl group, trifluoromethyl group, or tert-butyl group.

7. The method according to claim 1, wherein the ester compound is (2R,3R)-2-difluorophenyl-3-pivaloyloxy-1-(1H-1,2,4-triazol-1-yl)-butan-2-ol, and the alcohol compound is (2R,3R)-2-difluorophenyl-1-(1H-1,2,4-triazol-1-yl)-2,3-butanediol.

8. The method according to claim 1, wherein the ester compound is (2R,3R)-2-(2,4-difluorophenyl)-3-pivaloyloxy-1-(1H-1,2,4-triazol-1-yl)-butan-2-ol, and the alcohol compound is (2R,3R)-2-(2,4-difluorophenyl)-1-(1H-1,2,4-triazol-1-yl)-2,3-butanediol.

9. The method according claim 1, wherein an operational temperature during the passing of the solution is from 0° C. to 90° C.

10. The method according to claim 1, wherein in the passing of the solution, the solution is passed through the column such that a space velocity (SV) of the solution is from 0.01 to 100 hr$^{-1}$.

11. The method according to claim 1, wherein a total content of the ester compound, methanol, and ethanol in the solution is 80 mass % or more.

12. The method according to claim 1, wherein a solution obtained after the passing comprises the ester compound in an amount of 5 mass % or less in 100 mass % of the solution obtained after the passing.

13. The method according to claim 1, wherein the anion exchange resin having methoxide and/or ethoxide as a counter anion is produced by passing methanol and/or ethanol through a column packed with an anion exchange resin having a hydroxide ion as a counter anion.

14. The method according to claim 1, further comprising, prior to the passing of the solution:

passing methanol and/or ethanol through a column packed with an anion exchange resin having a hydroxide ion as a counter anion such that the anion exchange resin having methoxide and/or ethoxide as a counter anion is produced.

15. The method according to claim 14, wherein in the passing of methanol and/or ethanol, the methanol and/or ethanol is passed through the column such that a space velocity (SV) of the methanol and/or ethanol is from 0.01 to 100 hr$^{-1}$.

16. The method according to claim 1, wherein in the passing, the column is vertically positioned such that the solution is passed through the column upwardly or downwardly.

\* \* \* \* \*